US005783001A

United States Patent [19]
Sardelis et al.

[11] Patent Number: 5,783,001
[45] Date of Patent: Jul. 21, 1998

[54] PROCESS FOR THE HEAT TREATMENT OF SURGICAL NEEDLES BY AGING

[75] Inventors: Timothy Sardelis, Somerset, N.J.; Douglas Warren Ackerman, Gainesville, Ga.; William McJames, Belle Mead, N.J.

[73] Assignee: Ethicon, Inc., Somerville, N.J.

[21] Appl. No.: 748,845

[22] Filed: Nov. 14, 1996

[51] Int. Cl.[6] .............................. A61B 17/00; C21D 6/02; C21D 9/76

[52] U.S. Cl. ................................ 148/607; 606/222; 164/5

[58] Field of Search ................................ 606/222; 164/5; 148/607

[56] References Cited

U.S. PATENT DOCUMENTS

| | | | |
|---|---|---|---|
| 3,314,831 | 4/1967 | Hoenie et al. . | |
| 4,296,067 | 10/1981 | Nasman et al. | 422/26 |
| 4,660,559 | 4/1987 | McGregor et al. | 606/226 |
| 4,709,904 | 12/1987 | Schmetz | 266/250 |
| 4,959,068 | 9/1990 | Bendel et al. | 606/222 |
| 5,330,441 | 7/1994 | Prasad et al. . | |
| 5,358,577 | 10/1994 | Uehara et al. . | |
| 5,411,613 | 5/1995 | Rizk et al. . | |
| 5,533,982 | 7/1996 | Rizk et al. . | |

*Primary Examiner*—Christopher Kilner
*Attorney, Agent, or Firm*—Emil Richard Skula

[57] ABSTRACT

A method of heat treating and cleaning maraging or precipitation hardening stainless steel surgical needles is disclosed. The method comprises exposing the surgical needles to a partial vacuum at a temperature less than the aging temperature to remove volatile surface contaminants. Then the needles are heat treated in an argon gas environment at a pressure equal to or greater than 1.0 atmosphere.

14 Claims, 3 Drawing Sheets

PROCESS FOR THE HEAT TREATMENT OF SURGICAL NEEDLES BY AGING

TECHNICAL FIELD

The field of art to which this invention relates is heat treatment processes for heat treating surgical needles, in particular, precipitation hardening stainless steel surgical needles.

BACKGROUND OF THE INVENTION

Conventional surgical needles are typically made from stainless steels. The types of stainless steel which are used include Types 420SS, 455SS, 302SS, and certain proprietary alloys such as those disclosed in U.S. Pat. No. 5,000,912 which is incorporated by reference. Type 420SS stainless steel alloy is conventionally referred to as a martensitic stainless steel, while Type 302SS stainless steel alloy is referred to as an austenitic stainless steel. Type 455SS stainless steel alloys and the proprietary alloys disclosed in U.S. Pat. No. 5,000,912 are conventionally referred to as maraging or precipitation hardening stainless steel.

In a conventional surgical needle manufacturing process, wire is removed from a spool, straightened, and then cut into needle blanks. Optionally, the wire may be drawn to a finer diameter as it is removed from the spool. The needle blanks are then subjected to a variety of conventional forming, grinding and shaping processes to produce surgical needles having distal piercing points and proximal suture mounting sections (e.g., either channels or drilled holes). The needles may be tapered, and may have cutting edges. Conventional surgical needles are typically curved by bending the needle blanks, but may also have a straight configuration. Typically, portions of the surgical needles are flattened to assist in grasping the needles with conventional needle holding instruments.

It is known that stainless steel needles made from martensitic Type 420SS and maraging grades of stainless steel must be heat treated after the manufacturing process in order to improve the strength of the needle. For the Type 420SS grades, this heat treatment transforms the structure into martensite. While this transformation increases the mechanical strength of such needles, it is accomplished with an accompanying decrease in ductility. In order to improve the ductility of heat treated surgical needles made from Type 420SS stainless steel, the needles are subsequently tempered.

The strength of precipitation hardening alloys is increased by a process called aging. Aging is a thermal process wherein the metal is brought to an elevated temperature and held there for a specific amount of time. Both the time and temperature are of critical importance. If the time or the temperature vary from the optimum levels, the alloy may be under or over aged and not exhibit the best mechanical properties. The precipitation hardening alloys, unlike the martensitic alloys, do not need a secondary treatment after aging, since there is not typically a concomitant decrease in ductility.

Surgical needles made from precipitating alloys are typically batch aged in a furnace. The interior furnace atmosphere can be air, an inert or non-reactive gas, or a vacuum. Aging can also be done by immersing the surgical needles in a non-reactive molten salt or other liquid or solid medium which is at the aging temperature.

Although the conventional processes for aging surgical needles made from precipitation hardening alloys produce surgical needles having the desired ductility and strength, there are certain disadvantages associated with these processes, particularly the known vacuum processes.

One disadvantage relates to the difficulty in attaining a high temperature in a furnace while under a high vacuum. In a conventional vacuum heat treatment cycle during the vacuum phase, the interior of the furnace is heated only by radiation since there is little or no conductive medium to transfer the heat. This is an inefficient way to heat the furnace and transfer heat to the needles. Another difficulty is simultaneously maintaining a high vacuum and a high temperature. Yet another disadvantage is that the surfaces of the surgical needles may not be sufficiently clean when placed in the furnace. Aging a dirty or surface contaminated surgical needle may destroy the surface finish and result in diminished ease of penetration of the needle through tissue. Still yet another disadvantage of conventional vacuum heat treatment processes is that it is known that stainless steels held at elevated temperatures under vacuum for an extended time may exhibit a loss of the alloying element chromium. This is believed to have the effect of decreasing the corrosion resistance of the surgical needle in service.

Accordingly, there is a need in this art for improved aging processes which overcome these disadvantages.

DISCLOSURE OF THE INVENTION

Therefore, there is an object of this invention to provide a novel process which allows precipitation hardening surgical needles to be cleaned and heat treated utilizing the advantages of both a vacuum and an inert gas atmospheres.

It is a further object of the present invention to provide a heat treatment process for surgical needles which also includes a cleaning step prior to the aging step.

It is still yet a further object of the present invention to provide a heat treatment process which provides for more efficient heat treatment of precipitation hardening surgical needles.

Accordingly, a novel process for heat treating precipitation hardening stainless steel surgical needles is disclosed. In the initial step of the process, surgical needles are placed into a furnace. Next, the needles are exposed to a vacuum. While under the vacuum the needles are heated to a sufficient temperature for a sufficient amount of time to effectively clean or remove volatile contaminants from the surfaces of the needle, wherein the temperature is below the aging temperature. Optionally, the internal pressure of the furnace during the cleaning step is atmospheric. Next, an inert gas is injected into the furnace. The pressure of the inert gas is at least one atmosphere. The temperature of the needles is then raised to the aging temperature of the alloy by increasing the temperature within the furnace. As the temperature is increased the pressure of the inert gas inside the furnace is maintained at 760 Torr (1 atmosphere) or greater at the aging temperature. The needles are then held at the aging temperature for a sufficient time to effectively age harden the needles. The needles are then cooled and removed from the furnace.

Yet another aspect of the present invention is a novel process for heat treating precipitation hardening stainless steel surgical needles. In the initial step of the process, surgical needles are placed into a furnace. Next, the needles are exposed to a vacuum. While under the vacuum the needles are heated to a sufficient temperature for a sufficient period of time to effectively clean or remove volatile contaminants from the surfaces of the needle, wherein the temperature is below the aging temperature. Next, an inert gas is injected into the internal furnace chamber such that the internal chamber pressure is less than one atmosphere. The pressure of the inert gas is dependent on the cleaning temperature of the needles and the temperature at which the needles will be aged. The temperature of the needles is than raised to the aging temperature of the alloy. As the temperature is increased the pressure of the inert gas inside the furnace increases until it is at least 760 Torr (1 atmosphere) at the aging temperature. The needles are then held at the aging temperature for a sufficient time to effectively age harden the needles. The needles are then cooled and removed from the furnace.

The foregoing and other features and advantages of the present invention will become more apparent from the following description and accompanying drawings.

DESCRIPTION OF PREFERRED EMBODIMENTS

As previously mentioned hereinabove, U.S. Pat. No. 5,000,912 is incorporated by reference in its entirety herein.

Figure 1:
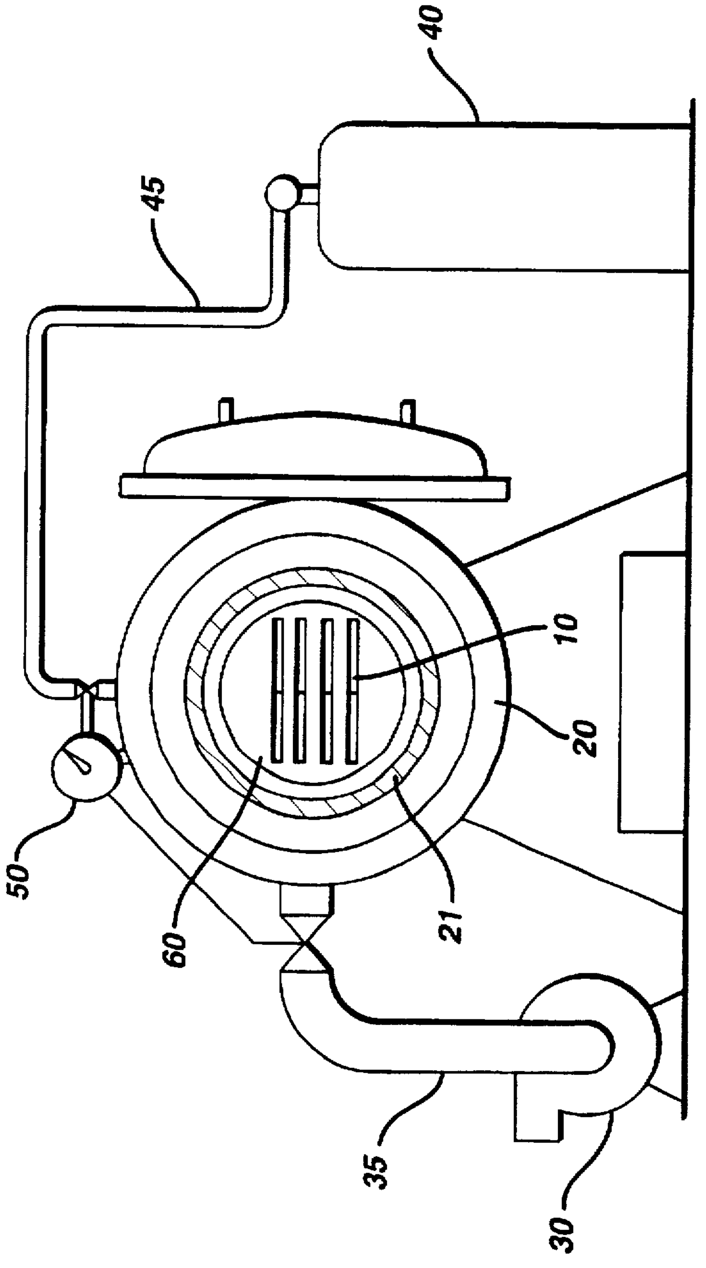
FIG. 1 is a schematic flow diagram of a heat treatment process of the present invention.

A schematic flow diagram of a process of the present invention is seen in FIG. 1. Untreated surgical needles 10 are placed into the internal chamber 21 of oven 20. Heat treatment oven 20 may be any conventional oven capable of withstanding both pressure and vacuum. Typically oven 20 will be able to withstand an internal vacuum of at least $1\times10^{-4}$ Torr and an internal pressure of up to about 850 Torr to about 4560 Torr. It is preferred that oven 20 be heated with electric heating elements, although any conventional heat source or heating element may be used. After the needles 10 are secured within oven 20, a vacuum is pulled upon the internal chamber 21 by vacuum pump 30 through pipe 35. Once the chamber 21 has been sufficiently evacuated to reach the desired vacuum, the temperature is increased and held at a sufficient temperature for a sufficient period of time to effectively clean the needles 10. Typically, the temperature will be about 25° C. to about 200° C., more typically about 50° C. to about 200 C., and preferably about 100 C. to about 200 C. Typically, the time of the cleaning phase will be about 1 minute to about 20 minutes, more typically about 2 minutes to about 10 minutes, preferably about 3 minutes to about 5 minutes. The vacuum pulled on chamber 21 will be sufficient to effectively volatize or clean any surface contamination on needles 10. Typically the vacuum will be about $2\times10^{-2}$ to about $1\times10^{-2}$ Torr, more typically about $2\times10^{-3}$ to about $1\times10^{3}$ Torr, and preferably about $2\times10^{-4}$ to about $1\times10^{4}$ Torr. The surface contaminants typically contained on the surfaces of a surgical needle during a manufacturing process which can be removed by this cleaning step include conventional contaminants which result from the needles manufacturing process including lubricating oils, greases and the like.

After the needles 10 have been cleaned, the chamber 21 is pressurized, preferably with a non-reactive or inert gas 40 through pipe 45. The inert gases which can be utilized are those which are conventionally used including gases such as include argon, nitrogen, and helium. It is particularly preferred to use argon. Although not preferred, and if one skilled in the art were willing to accept the attendant disadvantages, if any, air could be used to pressurize the furnace. Typically, the chamber will be pressured to a pressure of about 532 Torr to about 988 Torr, more typically about 608 Torr to about 912 Torr, and preferably about 684 Torr to about 836 Torr. In a preferred embodiment of the process of the present invention, the chamber is initially charged (prior to the heat treatment step) to a pressure of at least one atmosphere (760 Torr). The pressure in cavity 21 is maintained by pressure regulator 50 to maintain a desired pressure level during the heat treatment step. In an alternate embodiment, the pressure of the gas 40 in cavity 21 is calculated such that the chamber 21 pressure during the heat treatment step at the heat treatment temperature will be about 1.0 atmospheres without the need for a pressure regulator or control system. This is done using known gas algorithms, constants and factoring in the relevant particular physical parameters associated with furnace 20.

After the cavity is pressurized with gas 40, the heating elements 60 are energized to heat the gas to a sufficient temperature for a sufficient amount of time to effectively age the needles. Typically the heat treatment temperature will be about 350° C. to about 550° C., more typically about 400° C. to about 500° C., and preferably about 460° C. to about 490° C. The treatment time is typically about 15 minutes to about 20 hours, more typically about 30 minutes to about 10 hours, and preferably about 30 minutes to about 4 hours.

The following examples are illustrative of the principles and practice of the present invention, although not limited thereto.

EXAMPLE 1

Surgical needles made from Type 455SS stainless steel alloy were heat treated in accordance with a process of the present invention. Using a process of the present invention, the surgical needles were placed in a conventional furnace capable of withstanding both internal pressure and internal vacuum. A vacuum of $1\times10^{-1}$ Torr was applied to the furnace chamber. The chamber temperature was then raised to 200° C. to effectively remove any volatiles that were on the surfaces of the needles. The surgical needles were held at these levels of vacuum and temperature for about 5 minutes. After the cleaning process was completed, argon gas was introduced into the furnace chamber at 760 Torr (1.0 atmosphere). The temperature was then raised to 475° C. The surgical needles were then held at 475° C. for 4 hours. The chamber pressure was regulated during the heat treatment process by a conventional pressure regulator valve and control system. The furnace was then cooled to 60° C. by a flow of Argon gas through the furnace chamber. The heat treated, maraged (precipitation hardened) needles were then removed from the furnace for further processing.

EXAMPLE 2

Surgical needles made from Type 455SS stainless steel alloy were heat treated in accordance with a process of the present invention. Type-455SS is a precipitation aging or hardening alloy whose aging treatment is 475° C. maintained for 4 hours. Using this process, the surgical needles were placed in a conventional furnace capable of withstanding both internal pressure and internal vacuum. A vacuum of $1\times10^{-4}$ Torr was applied to the furnace chamber. The chamber temperature was then raised to 200° C. to effectively remove any volatiles that were on the surfaces of the needles. The surgical needles were held at these levels of vacuum and temperature for 3 to 5 minutes. After the cleaning process was completed, Argon gas was introduced into the furnace chamber at 479 Torr (0.63 atmospheres). The temperature was then raised to 475° C. Based on the General Gas Law the internal pressure of the chamber was approximately 760 Torr (1 atmosphere) at the aging temperature of 475° C. The surgical needles were then held at 475° C. for 4 hours. The furnace was then cooled to 60° C. by a flow of Argon gas through the furnace chamber. The heat treated, maraged (precipitation hardened) needles were then removed from the furnace for further processing.

Figure 2:
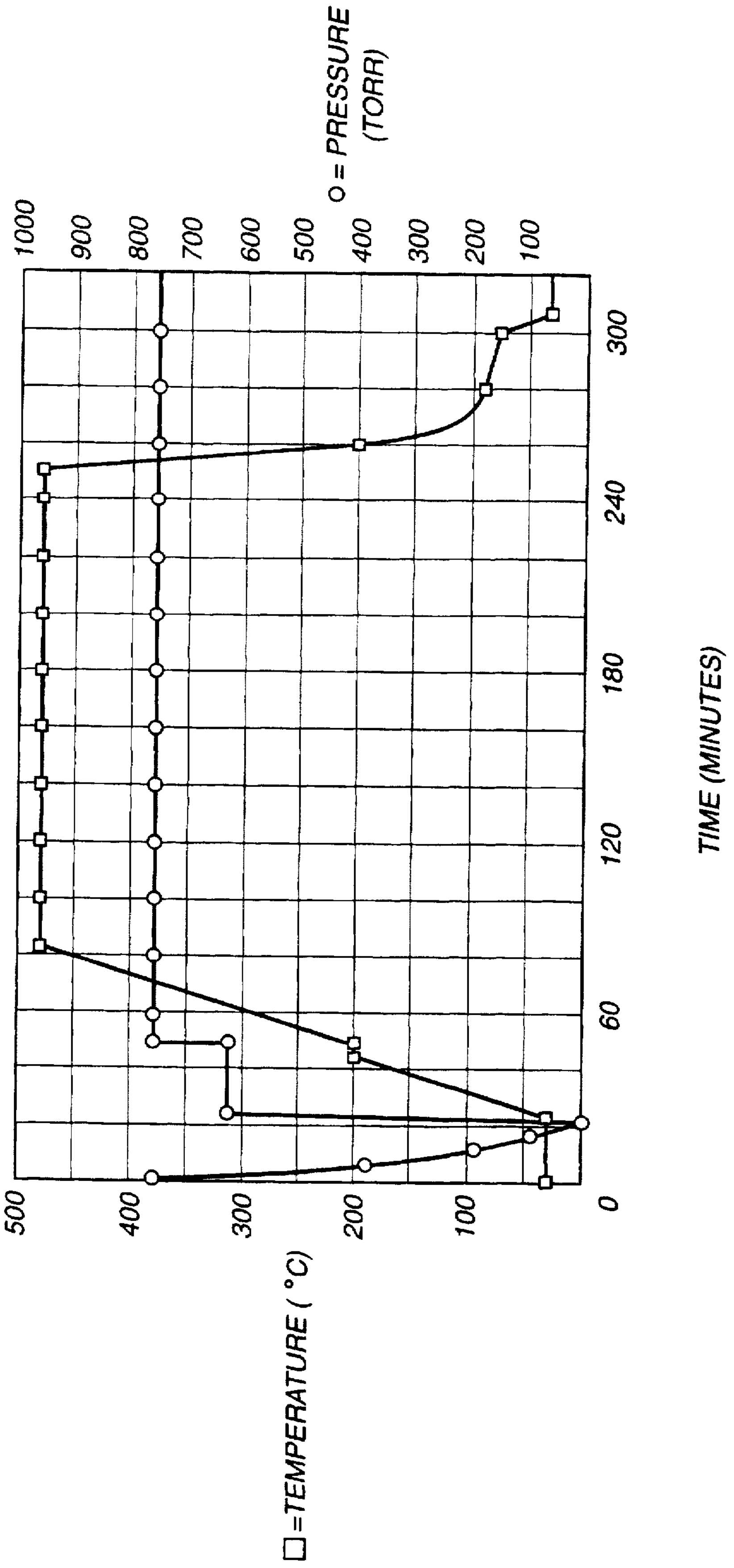
FIG. 2 is a graph of a preferred heat treatment cycle of the process of the present invention.

A preferred embodiment of a process of the present invention is illustrated in the diagram of FIG. 2. The attached FIG. 2 shows the process parameters of pressure and temperature for the cycle. In FIG. 2, with the surgical needles sealed in the chamber of a furnace, at room temperature, the pressure is lowered to $1\times10^{-1}$. When that vacuum level has been attained, the temperature in the chamber is increased to 200° C. and held there for a sufficient period of time, 5 minutes, which will effectively clean the needles. Then the chamber pressure is increased to at least 1.0 atmospheres by introducing additional argon gas. The temperature is then raised to the aging temperature, in this case, 475° C. After about 60–165 minutes, the furnace and needles are cooled to room temperature under argon gas at about one atmosphere pressure. The cycle is then complete.

Figure 3:
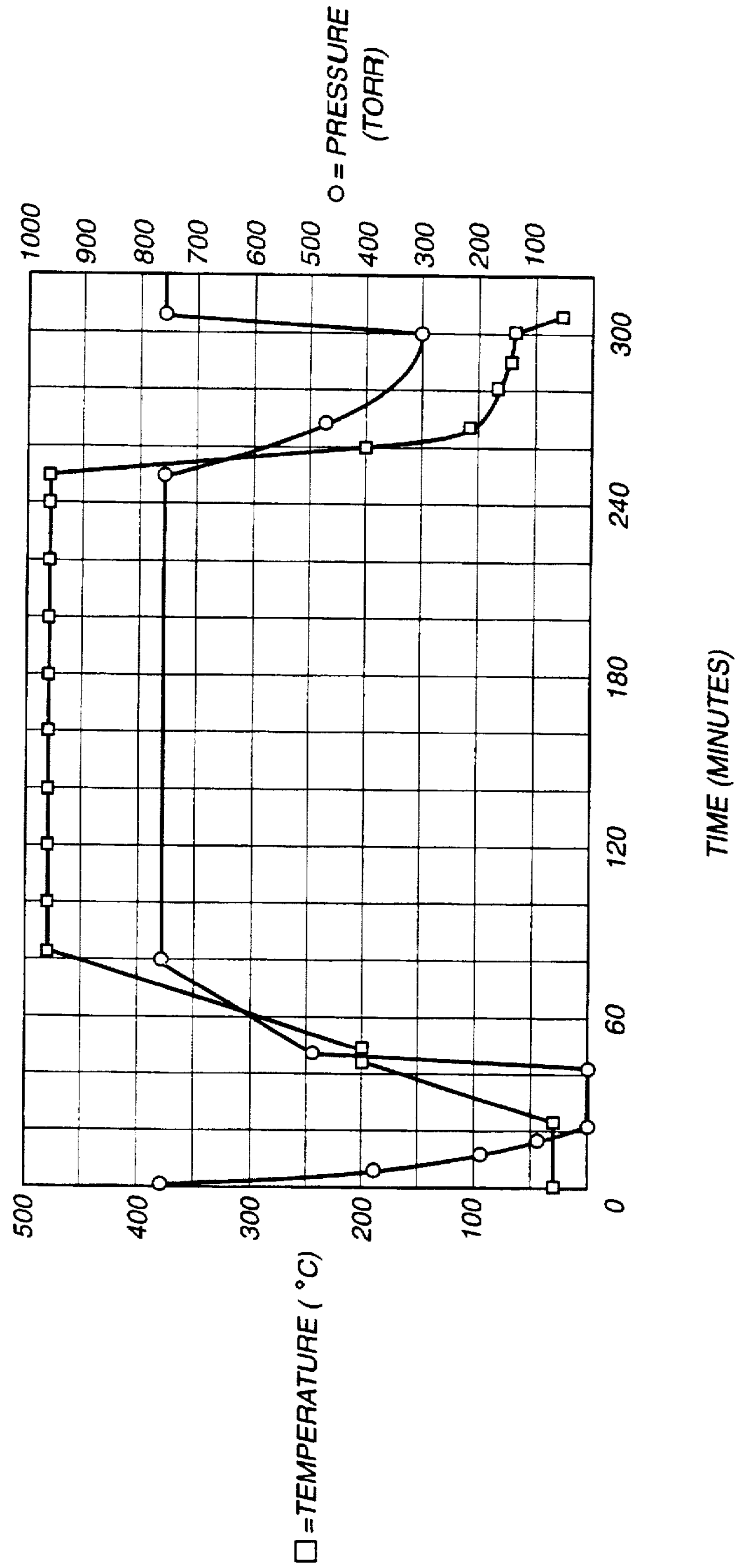
FIG. 3 is a graph of an alternate embodiment of a heat treatment process of the present invention.

An alternate embodiment of a heat treatment cycle of the present invention is seen in FIG. 3. The attached FIG. 3 show the process parameters of pressure and temperature. In FIG. 3, after surgical needles are sealed in the chamber of a furnace, at room temperature, the pressure is lowered to $1\times10^{-4}$. When that vacuum level has been attained the temperature in the chamber is increased to 200° C. and held there for a period of time which will clean the needles, about 3 to 5 minutes. After the cleaning phase is completed, argon gas in introduced into the chamber of the furnace at 479 Torr (0.63 atmospheres), the temperature being held constant. The temperature is then raised to the aging temperature, in this case, 475° C. The gas enclosed in the chamber expands according to the General Gas Law. At the aging temperature the surgical needles are at 475° C. and 760 Torr (1 atmosphere). After 4 hours the argon gas is again introduced and the furnace is cooled to room temperature. The cycle is then complete.

There are many advantages of heat treatment process of the present invention when compared to the prior art heat treatment processes. The advantages include better and more efficient heat transfer, uniformity of heating, the ability to reduce oxide contamination on the surface of the needles, and the ability to more efficiently pull off volatiles from the surfaces of the needles.

Although this invention has been shown and described with respect to detailed embodiments thereof, it will be understood by those skilled in the art that various changes in form and detail thereof may be made without departing from the spirit and scope of the claimed invention.

We claim:

1. A method of heat treating precipitation hardening stainless steel surgical needles, the method comprising the steps of:

exposing and subjecting a plurality of precipitation hardening stainless steel surgical needles having outer surfaces to a sufficient vacuum and a sufficient temperature in a furnace to effectively remove volatile surface contaminants from the outer surfaces of the needles;

exposing the needles to an inert gas wherein the pressure of the gas is at least ambient;

heating the gas to a sufficient temperature and maintaining the gas at said temperature for a sufficient amount of time to effectively heat treat the needles; and, lowering the temperature of the gas to reduce the temperature of the needles to ambient temperature.

2. The method of claim 1 wherein the vacuum in the initial cleaning step is about $2\times10^{-2}$ Torr to about $1\times10^{-4}$ Torr.

3. The method of claim 1 wherein the temperature in the cleaning step is about 25° C. to about 200° C.

4. The method of claim 1 wherein the pressure in the heat treatment step is about 684 Torr to about 836 Torr.

5. The method of claim 1 wherein the temperature in the heat treatment step is about 350° C. to about 550° C.

6. A method of heat treating and cleaning precipitation hardening stainless steel surgical needles, the method comprising the steps of:

exposing and subjecting a plurality of precipitation hardening stainless steel surgical needles having outer surfaces to a sufficient vacuum and a sufficient temperature in a furnace to effectively remove volatile surface contaminants from the outer surfaces of the needles, wherein the temperature is below the heat treatment temperature;

exposing the needles to an inert gas wherein the pressure of the gas is less than ambient;

heating the gas to a sufficient temperature and maintaining the gas at said temperature at a pressure of 1.0 atmospheres for a sufficient amount of time to effectively heat treat the needles; and, lowering the temperature of the gas to reduce the temperature of the needles to ambient temperature.

7. The method of claim 6 wherein the vacuum in the initial cleaning step is about $2\times10^{-2}$ Torr to about $1\times10^{-4}$ Torr.

8. The method of claim 6 wherein the temperature in the cleaning step is about 25° C. to about 200° C.

9. The method of claim 6 wherein the pressure in the heat treatment step is about 684 Torr to about 836 Torr.

10. The method of claim 1 wherein the temperature in the heat treatment aging step is about 350° C. to about 550° C.

11. The method of claim 1 wherein the stainless steel needles comprise Type 455SS stainless steel alloy.

12. The method of claim 6 wherein the stainless steel needles comprise Type 455SS stainless steel alloy.

13. The method of claim 1 wherein the stainless steel alloy is a precipitation hardening stainless steel alloy.

14. The method of claim 6 wherein the stainless steel alloy is a precipitation hardening stainless steel alloy.

* * * * *